US012669487B2

(12) United States Patent
Nelson, Jr. et al.

(10) Patent No.: US 12,669,487 B2
(45) Date of Patent: Jun. 30, 2026

(54) OPTICAL HYDROGEN DETECTOR EMPLOYING CONTROLLED WATER VAPOR CONCENTRATION OVER CATALYST

(71) Applicant: Aerodyne Research, Inc., Billerica, MA (US)

(72) Inventors: David D. Nelson, Jr., N. Chelmsford, MA (US); Scott C. Herndon, Littleton, MA (US); Joanne H. Shorter, Lexington, MA (US); Joseph R. Roscioli, Chelmsford, MA (US); Elizabeth M. Lunny, North Billerica, MA (US); Richard A. Wehr, Arlington, MA (US)

(73) Assignee: Aerodyne Research, Inc., Billerica, MA (US)

( * ) Notice: Subject to any disclaimer, the term of this patent is extended or adjusted under 35 U.S.C. 154(b) by 268 days.

(21) Appl. No.: 18/526,541

(22) Filed: Dec. 1, 2023

(65) Prior Publication Data

US 2024/0094178 A1     Mar. 21, 2024

Related U.S. Application Data

(60) Continuation-in-part of application No. 18/080,818, filed on Dec. 14, 2022, now Pat. No. 12,292,428,
(Continued)

(51) Int. Cl.
*G01N 33/00*          (2006.01)

(52) U.S. Cl.
CPC ....... *G01N 33/005* (2013.01); *G01N 33/0013* (2013.01); *G01N 33/0016* (2013.01)

(58) Field of Classification Search
CPC ............. G01N 33/005; G01N 33/0013; G01N 33/0016
See application file for complete search history.

(56) References Cited

U.S. PATENT DOCUMENTS 3,549,327 A    12/1970  Fergusson
4,766,081 A *   8/1988  Ruckert ................. G01N 22/00
                                                          436/171
(Continued)

FOREIGN PATENT DOCUMENTS

CN         201811870 U      4/2011
CN         111007031 A      4/2020
(Continued)

OTHER PUBLICATIONS

JP-H10160696-A (Year: 1998).*
(Continued)

*Primary Examiner* — Fatemeh Esfandiari Nia
(74) *Attorney, Agent, or Firm* — Cesari and McKenna, LLP; James A. Blanchette

(57)          ABSTRACT

In various embodiments, both very high speed and very high sensitivity hydrogen detection is achieved by controlling water vapor concentration over the catalyst used to convert hydrogen in sample gas (e.g., ambient air) to water vapor, to provide a substantially stable water vapor mixing level at a target mixing ratio. The naturally-occurring water vapor in the sample gas, without further steps, typically would vary over time within a wide range (e.g., due to changing atmospheric conditions). By controlling a level of water vapor over the catalyst to be substantially equal to a target mixing ratio that is not too low as to impair response time, and not too high as to impair sensitivity, both very high speed and very high sensitivity can be provided.

20 Claims, 9 Drawing Sheets

Related U.S. Application Data which is a division of application No. 17/178,696, filed on Feb. 18, 2021, now Pat. No. 11,802,858.

(56) References Cited

U.S. PATENT DOCUMENTS

| | | | |
|---|---|---|---|
| 6,897,960 | B2 | 5/2005 | DiMeo, Jr. et al. |
| 7,255,836 | B2 | 8/2007 | Lehmann et al. |
| 7,277,177 | B2 | 10/2007 | Augustine et al. |
| 7,852,480 | B2 | 12/2010 | Uchiyama |
| 8,448,493 | B2 | 5/2013 | McIntyre et al. |
| 9,322,969 | B2 | 4/2016 | Burov et al. |
| 11,561,324 | B1 | 1/2023 | Burba |
| 11,802,858 | B2 | 10/2023 | Nelson, Jr. et al. |
| 2002/0154310 | A1 | 10/2002 | DiMeo, Jr. et al. |
| 2003/0082417 | A1 | 5/2003 | Lillis |
| 2004/0023595 | A1 | 2/2004 | Ping et al. |
| 2004/0107764 | A1 | 6/2004 | Yan |
| 2004/0193379 | A1 | 9/2004 | Lillis et al. |
| 2005/0272167 | A1 | 12/2005 | Andino |
| 2007/0240488 | A1 | 10/2007 | Kreuser et al. |
| 2011/0174052 | A1 | 7/2011 | Kuebel |
| 2013/0059395 | A1 | 3/2013 | Alvarez et al. |
| 2013/0145819 | A1* | 6/2013 | Odell ........................ G01N 1/24 |
| | | | 73/23.2 |
| 2017/0023475 | A1 | 1/2017 | Dam et al. |
| 2017/0184537 | A1 | 6/2017 | Umasankar et al. |
| 2019/0263699 | A1 | 8/2019 | Finger et al. |
| 2019/0391045 | A1 | 12/2019 | Yoshimura |
| 2020/0033301 | A1 | 1/2020 | Cardin |
| 2020/0249184 | A1* | 8/2020 | Matsukura ........... G01N 33/005 |
| 2021/0293768 | A1 | 9/2021 | Johnson et al. |
| 2022/0187203 | A1 | 6/2022 | Zondlo et al. |
| 2022/0260537 | A1 | 8/2022 | Nelson, Jr. et al. |
| 2023/0116043 | A1 | 4/2023 | Nelson, Jr. et al. |
| 2023/0152220 | A1 | 5/2023 | Nelson, Jr. et al. |

FOREIGN PATENT DOCUMENTS

| | | |
|---|---|---|
| CN | 108562017 B | 11/2020 |
| EP | 2140249 B1 | 9/2011 |
| GB | 1017940 A | 1/1966 |
| JP | S-49-026920 B1 | 7/1974 |
| JP | S60-80755 A | 5/1985 |
| JP | H07-325075 A | 12/1995 |
| JP | H10160696 A * | 6/1998 |
| JP | 2006-179224 A | 7/2006 |
| JP | 2011-257319 A | 12/2011 |
| JP | 6641218 B2 | 2/2020 |
| WO | 2011/155086 A1 | 12/2011 |
| WO | 2013005332 A1 | 1/2013 |
| WO | WO-2020/172541 A1 | 8/2020 |

OTHER PUBLICATIONS

Chtanov, A., et al., "Differential Optical Detection of Hydrogen Gas in the Atmosphere," Elsevier Sciences B.V., Elsevier, Sensors and Actuators, vol. 79, Issue 2-3, Oct. 15, 2001, pp. 196-199.
CN-108562017-B-eng (Year: 2020).
"Halo H2: Trace-Level Hydrogen Analyzer," Tiger Optics, Tiger Optics, LLC, May 2020, pp. 1-2.
"Halo H2: Trace-Level Hydrogen Analyzer," Tiger Optics, Tiger Optics, LLC, Oct. 2021, pp. 1-2.
JP-6641218-B2-eng (Year: 2020).
L'Vov, Boris V., et al., "Catalytic Oxidation of Hydrogen on Platinum," Springer, Akadémiai Kiadó, Budapest Hungary, Journal of Thermal Analysis Calorimetry, Sep. 7, 2012, pp. 1-8.
"Notification of Transmittal of the International Search Report and the Written Opinion of the International Searching Authority, or the Declaration," International Filing Date: Jan. 27, 2022, International Application No. PCT/US2022/014073, Applicant: Aerodyne Research, Inc., Date of Mailing: Jun. 21, 2022, pp. 1-19.
Rizzolo, Serena, et al., "Distributed and Discrete Hydrogen Monitoring Through Optical Fiber Sensors Based on Optical Frequency Domain Reflectometry," IOP Publishing Ltd, JPhys Photonics, vol. 2, Jan. 28, 2020, pp. 1-7.
Rollins, A. W., et al., "Catalytic Oxidation of $H_2$ on Platinum: A robust Method for Generating Low Mixing Ratio $H_2O$ Standards," Copernicus Publications, Atmospheric Measurement Techniques, vol. 4, Oct. 4, 2011, pp. 2059-2064.
Shin, Woosuck et al., "Hydrogen-Selective Thermoelectric Gas Sensor", Sensors an Actuators B: Chemical, Elsevier B.V., NL, vol. 93, No. 1-3, Aug. 1, 2003, pp. 304-308.
Shin, Woosuck et al., "Integration of Ceramic Catalyst on Micro-Thermoelectric Gas Sensor", Sensors an Actuators B: Chemical, Elsevier B.V., NL, vol. 118, No. 1-2, Oct. 25, 2006, pp. 283-291.
"Notification of Transmittal of the International Search Report and the Written Opinion of the International Searching Authority, or the Declaration," International Filing Date: Nov. 6, 2024, International Application No. PCT/US2024/054734, Date of Mailing: Jan. 27, 2025, pp. 1-13.
English Translation of CN-201811870-U (Year: 2011).
English Translation of WO-2013005332-A1 (Year: 2013).
"Notification of Transmittal of the International Search Report and the Written Opinion of the International Searching Authority, or the Declaration," International Filing Date: Oct. 31, 2023, International Application No. PCT/US2023/036493, Date of Mailing: Feb. 26, 2024, pp. 1-12.

* cited by examiner

OPTICAL HYDROGEN DETECTOR EMPLOYING CONTROLLED WATER VAPOR CONCENTRATION OVER CATALYST

RELATED APPLICATIONS

The present application is a continuation-in-part of U.S. patent application Ser. No. 18/080,818, now issued as U.S. Pat. No. 12,292,428, filed on Dec. 14, 2022, by David D. Nelson, Jr. et al for a "Rapid, Sensitive Hydrogen Detector with Active Hydrogen Derived Water Vapor Signal Modulation", which is a divisional of U.S. patent application Ser. No. 17/178,696, now issued as U.S. Pat. No. 11,802,858, filed on Feb. 18, 2021, by David D. Nelson, Jr. et al for a "Rapid, Sensitive Hydrogen Detector", the contents of both of which are incorporated by reference herein in their entirety, now issued as U.S. Pat. No. 11,802,858.

BACKGROUND

Technical Field

The present disclosure relates generally to gas detection, and more particularly to detection of molecular hydrogen.

Background Information

As the world transitions away from fossil fuels as our primary energy source, it is likely that a hydrogen-based energy infrastructure will emerge. For economic, safety and environmental impact reasons it will be essential to have effective ways of detecting molecular hydrogen ($H_2$). For example, to detect hydrogen gas leaks early before they can cause significant safety problems it will be essential to have effective ways of detecting molecular hydrogen in a sample gas (e.g., ambient air).

Optical absorption spectroscopy (e.g., laser absorption spectroscopy, non-dispersive infrared (NDIR) absorption spectroscopy, etc.) is a powerful technique for quantifying many small molecules. Molecular hydrogen, however, is difficult to directly detect using optical absorption spectroscopy because hydrogen has no rotational spectrum, has only a very weak vibration spectrum, and has electronic transitions only at very short and inaccessible wavelengths. To overcome this challenge, techniques have been developed to indirectly detect hydrogen using optical absorption spectroscopy. Some of these techniques first convert molecular hydrogen in a sample gas (e.g., ambient air) to water vapor using a catalyst, and then detect the water vapor, using it as a proxy for the hydrogen. Herein, molecular hydrogen in original sample gas is referred to as "sample molecular hydrogen" and water vapor produced from molecular hydrogen in the original sample gas is referred to as "sample hydrogen-derived water vapor."

Sample gas (e.g., ambient air) typically includes some water vapor that is a product of the natural environment or produced from sources other than the molecular hydrogen being measured (referred to herein collectively as "naturally-occurring water vapor"). Fortunately, techniques have been developed that may differentiate between naturally-occurring water vapor and sample hydrogen-derived water vapor.

There is an increasing desire by environmental researchers and the energy industry for higher speed and more sensitive techniques for measuring molecular hydrogen. However, when attempting to achieve very high speeds and very high sensitivity with detectors that rely upon conversion of molecular hydrogen to water vapor, unexpected challenges have been encountered. In this context, the term "very high speed" refers to a response time less than or equal to 10 seconds (s), and "very high sensitivity" refers to an ability to detect concentrations less than or equal to 10 part per billion (ppb). There seems to be a tension between achieving very high speed and very high sensitivity. It has not been understood why this is the case, and what, if anything, can be done so that both very high speed and very high sensitivity detection could both be consistently achieved. As a result, existing approaches have failed to provide the type of molecular hydrogen detection that is required to quantify and thereby minimize many types of hydrogen leakage, including leakage into the atmosphere.

Accordingly, there is need for improved techniques that can consistently achieve very high speed and very high sensitivity hydrogen detection.

SUMMARY

In various embodiments, both very high speed and very high sensitivity molecular hydrogen detection is achieved by controlling water vapor concentration over the catalyst used to convert sample molecular hydrogen to water vapor, to provide a substantially stable water vapor mixing level at a target mixing ratio. The naturally-occurring water vapor in the sample gas, without further steps, typically would vary over time within a wide range (e.g., due to changing atmospheric conditions). By controlling a level of water vapor over the catalyst to be substantially equal to a target mixing ratio that is not too low as to impair response time, and not too high as to impair sensitivity, both very high speed and very high sensitivity can be provided. In various embodiment, the target mixing ratio is selected to be a value between 1 ppm and 60 ppm, and preferably a value between 3 ppm and 30 ppm, such as 10 ppm.

The target mixing ratio may be achieved in a variety of different manners. In some embodiments, the target mixing ratio is achieved through water reduction. In a water reduction approach, water vapor is precisely removed from sample gas (e.g., ambient air) to achieve a level of controlled water vapor at the target mixing ratio. As used herein the term "controlled water vapor" refers to water vapor that is a product of the natural environment or produced from sources other than the sample molecular hydrogen that is subject to management or control. In other embodiments, the target mixing ratio is achieved through water addition. In a water addition approach, substantially all water vapor is removed from sample gas and a precise amount of water vapor is added back to achieve a level of controlled water vapor at the target mixing ratio. In still other embodiments, the target mixing ratio is achieved through hydrogen addition. In a hydrogen addition approach, instead of directly adding water vapor, a precise amount of a mixture containing hydrogen (or a hydrogen-containing water-convertible species) is added to the sample gas. Substantially all the water vapor is removed from the sample gas, and the hydrogen (or hydrogen-containing water-convertible species) is converted by the catalyst to water vapor to achieve a level of controlled water vapor at the target mixing ratio. While all approaches may be usable in different situations, a hydrogen addition approach may have a number of practical advantages over water reduction and direct water addition approaches.

In one embodiment, a method is provided for detecting molecular hydrogen. Sample gas is received that includes naturally-occurring water vapor and sample molecular hydrogen. A level of water vapor in the sample gas is controlled to be substantially equal to a target mixing ratio, wherein the target mixing ratio is selected as a value between 1 ppm and 60 ppm. Hydrogen in the sample gas is converted to additional water vapor to produce converted sample gas, and water vapor in the converted sample gas is measured to produce a water vapor signal. The water vapor signal is separated in the time domain into a controlled water vapor signal that describes controlled water vapor and a sample hydrogen-derived water vapor signal that describes sample hydrogen-derived water vapor, and a hydrogen signal that describes sample molecular hydrogen in the sample gas that is based on the sample hydrogen-derived water vapor signal is output.

In another embodiment, a molecular hydrogen detector is provided. The molecular hydrogen detector includes an inlet configured to receive sample gas that includes naturally-occurring water vapor and sample molecular hydrogen. The molecular hydrogen detector further includes a gas dyer to dry the sample gas. The molecular hydrogen detector further includes a flow controller configured to add an amount of humid gas to the sample gas or an amount of a mixture containing hydrogen or a hydrogen-containing water-convertible species to the sample gas to produce controlled water vapor, to cause a level of controlled water vapor in the sample gas to be substantially equal to a target mixing ratio. The molecular hydrogen detector further includes a catalytic oven having a catalyst configured to convert hydrogen in the sample gas to water vapor to produce converted sample gas, and an optical detection cell configured to use optical absorption spectroscopy to measure water vapor in the converted sample gas to produce a water vapor signal. The molecular hydrogen detector still further includes a processor configured to separate the water vapor signal in the time domain into a controlled water vapor signal that describes the controlled water vapor and a sample hydrogen-derived water vapor signal that describes sample hydrogen-derived water vapor, and to output a hydrogen signal that describes sample molecular hydrogen in the sample gas that is based on the sample hydrogen-derived water vapor signal.

In still another embodiment, a method is provided for detecting molecular hydrogen. Sample gas is received that includes naturally-occurring water vapor and sample molecular hydrogen, and the sample gas is dried. An amount of a mixture containing hydrogen or a hydrogen-containing water-convertible species is added to the sample gas. Hydrogen in the sample gas is converted to water vapor to produce converted sample gas having a level of controlled water vapor substantially equal to a target mixing ratio, wherein the converting converts both the sample molecular hydrogen and hydrogen or hydrogen-containing water-convertible species of the added mixture to water vapor, and the hydrogen or hydrogen-containing water-convertible species of the added mixture becomes controlled water vapor. Water vapor in the converted sample gas is measured to produce a water vapor signal. The water vapor signal is separated in the time domain into a controlled water vapor signal that describes the controlled water vapor and a sample hydrogen-derived water vapor signal that describes sample hydrogen-derived water vapor, and a hydrogen signal that describes sample molecular hydrogen in the sample gas that is based on the sample hydrogen-derived water vapor signal is output.

In yet another embodiment, a molecular hydrogen detector is provided. The molecular hydrogen detector includes means for receiving sample gas that includes naturally-occurring water vapor and sample molecular hydrogen, means for drying the sample gas, and means for adding an amount of a mixture containing hydrogen or a hydrogen-containing water-convertible species to the sample gas. The molecular hydrogen detector further includes means for converting hydrogen in the sample gas to water vapor to produce converted sample gas having a level of controlled water vapor substantially equal to a target mixing ratio, wherein the means for converting is configured to convert both the sample molecular hydrogen and hydrogen or hydrogen-containing water-convertible species of the added mixture to water vapor and the hydrogen or hydrogen-containing water-convertible species of the added mixture becomes controlled water vapor. The molecular hydrogen detector further includes means for measuring water vapor in the converted sample gas to produce a water vapor signal. The molecular hydrogen detector still further includes means for separating the water vapor signal in the time domain into a controlled water vapor signal that describes the controlled water vapor and a sample hydrogen-derived water vapor signal that describes sample hydrogen-derived water vapor, and for outputting a hydrogen signal that describes sample molecular hydrogen in the sample gas that is based on the sample hydrogen-derived water vapor signal.

It should be understood that a wide variety of additional features and alternative embodiments may be implemented other than those discussed in this Summary. This Summary is intended simply as a brief introduction to the reader for the further description that follows and does not indicate or imply that the examples mentioned herein cover all aspects of the disclosure or are necessary or essential aspects of the disclosure.

BRIEF DESCRIPTION OF THE DRAWINGS

The detailed description refers to the accompanying drawings of various embodiments, of which.

5

Figure 5A:
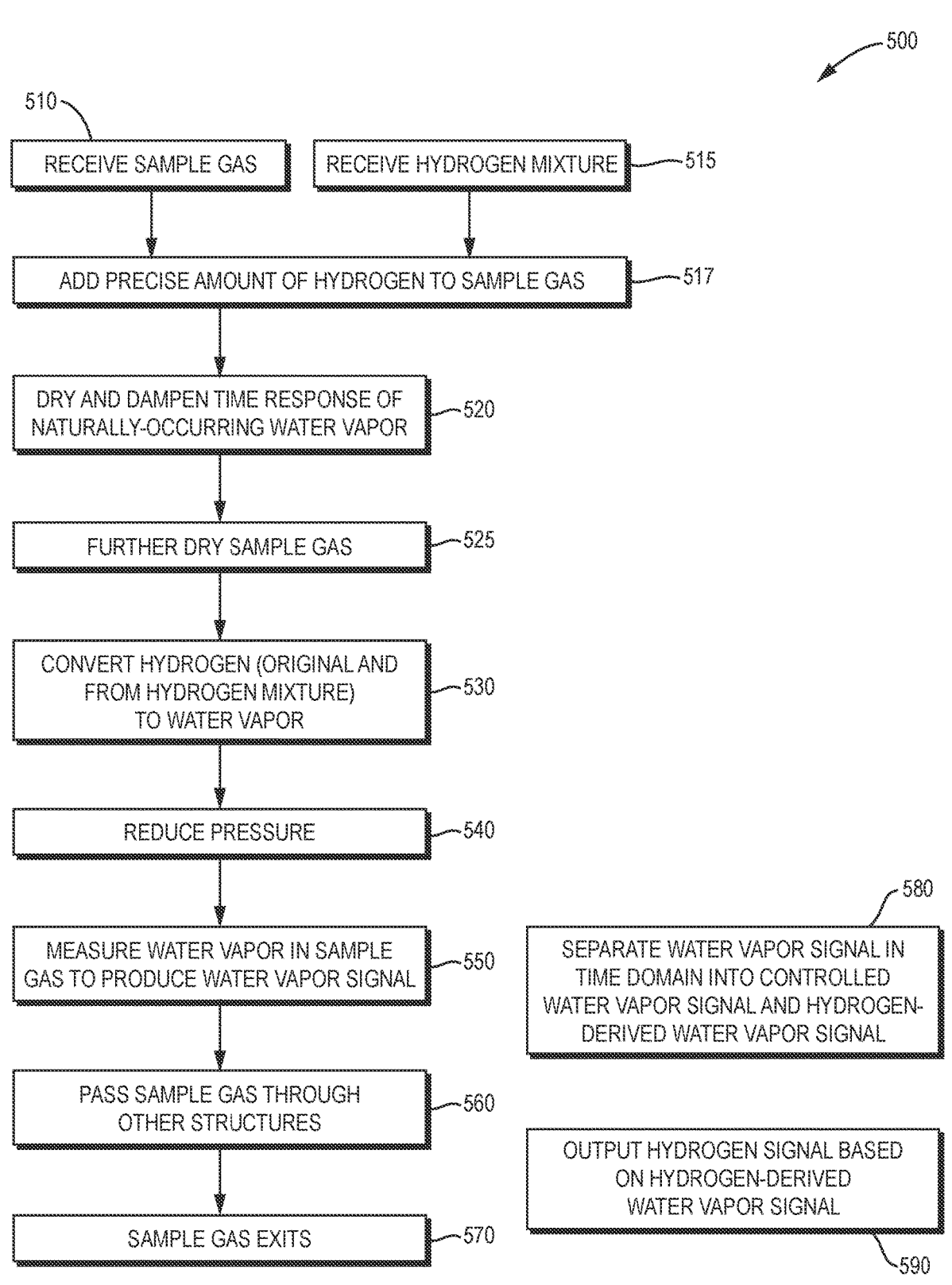
FIG. 5A is a flow diagram of an example sequence of steps for detecting molecular hydrogen in which a level of water vapor over a catalyst is controlled using a hydrogen
Figure 5B:
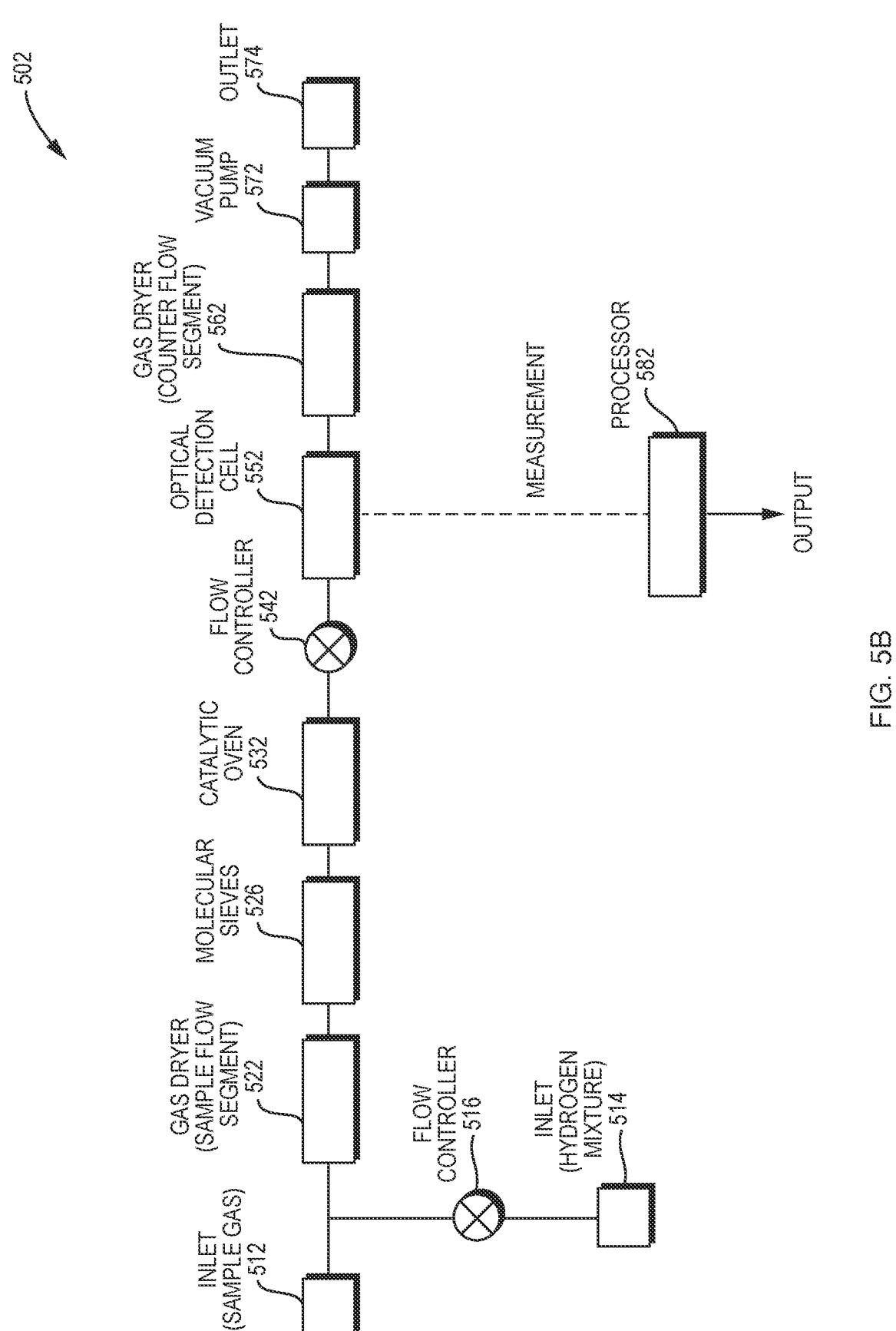

6 addition approach where a precise amount of hydrogen (or a hydrogen-containing water-convertible species) is added to the sample gas, substantially all the water vapor is removed from the sample gas, and the hydrogen (or a hydrogen-containing water-convertible species) is converted by the catalyst to water vapor to achieve the target mixing ratio; and FIG. 5B is a block diagram of an example improved optical hydrogen detector with components that may implement the sequence of steps in FIG. 5A.

DETAILED DESCRIPTION

The following description describes various embodiments. Any references to items in the singular should be understood to include items in the plural, and vice versa, unless explicitly stated or otherwise clear from the context. Grammatical conjunctions are intended to express any and all disjunctive and conjunctive combinations of conjoined clauses, sentences, words, and the like, unless otherwise stated or clear from the context. For example, the term "or" should be understood to mean "and/or." Any recitations of ranges of values are not intended to be limiting, are provided as examples only, and are not intended to constitute a limitation on the scope of the described embodiments. Further, any recitation of ranges should be interpreted as referring individually to any and all values falling within the range, unless otherwise indicated, and each separate value within such the range should be treated as if it were individually recited. Terms of approximation such as "about," "approximately," "substantially" or the like, should be construed as referring to an allowance for deviation that is customary in the field of the art. Absent specific reference to an alternative allowance for deviation that is customary in the field of the art, the allowance for deviation should be interpreted to be ±20% of the stated quantity where terms of approximation such as "about," "approximately," "substantially" and the like are used. Terms of relative ordering or orientation, such as "first," "last," "greatest", "lowest", "top," "bottom," and the like, should be understood to be used relative to a selected standard of comparison or perspective, and do not preclude differing orderings or orientations based on different standards of comparison or perspectives. No language in the description should be construed as indicating an element is a necessary or essential aspect of the disclosure.

Figure 1A:
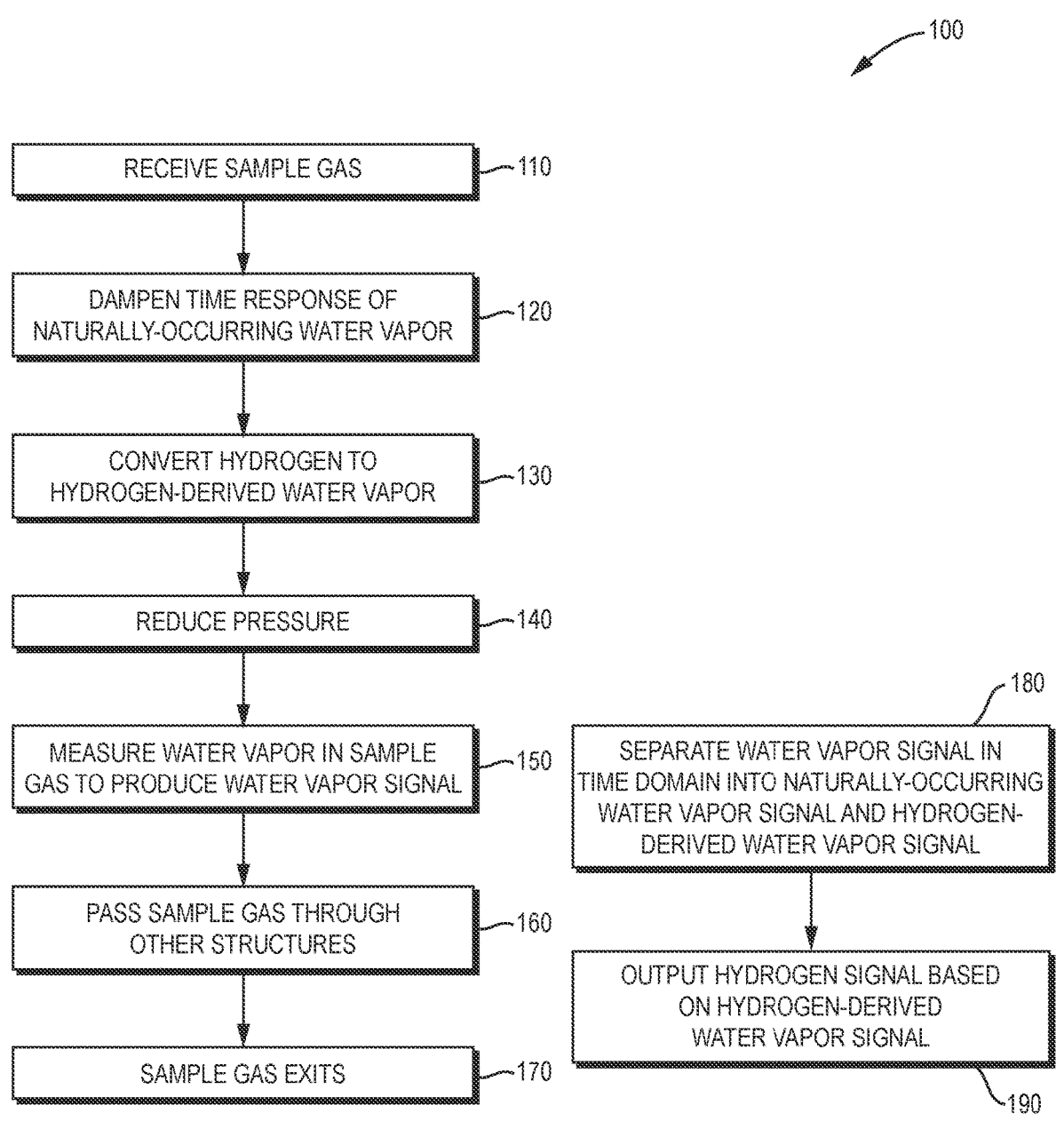
FIG. 1A is a flow diagram of an example sequence of steps for detecting molecular hydrogen in which water vapor level over a catalyst is allowed to vary over time within a wide range.
Figure 1B:
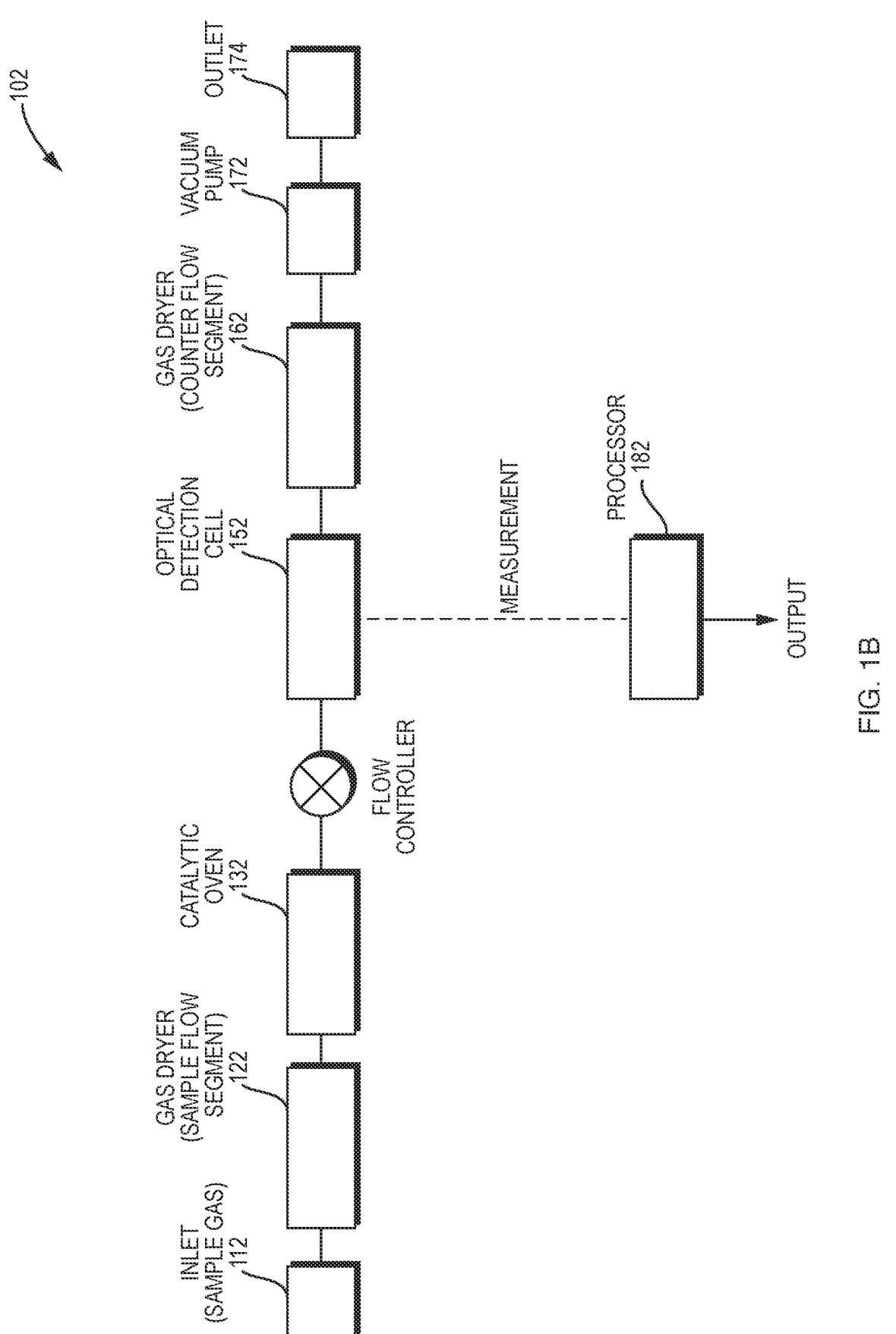
FIG. 1B is a block diagram of an example optical hydrogen detector with components that may implement the sequence of steps in FIG. 1A.

FIG. 1A is a flow diagram of an example sequence of steps 100 for detecting molecular hydrogen in which water vapor level over a catalyst is allowed to vary over time within a wide range. FIG. 1B is a block diagram of an example optical hydrogen detector 102 with components that may implement the sequence of steps 100 in FIG. 1A. As explained in more detail below, such a design may struggle to consistently achieve both very high speed and very high sensitivity.

At step 110, the optical hydrogen detector 102 receives sample gas (e.g., ambient air) that includes naturally-occurring water vapor and sample molecular hydrogen. The sample gas may be received via an inlet 112. Naturally-occurring water vapor in the sample gas may vary over time within a wide range (e.g., due to changing atmospheric conditions). For example, it may vary between amounts as low as 10 ppm and up to amounts as high as 50,000 ppm for ambient air, depending on the location and other environment factors. Absent a hydrogen source (e.g., a hydrogen leak), sample molecular hydrogen typically is quite low. For example, it may be about 0.5 ppm in ambient air.

At step 120, time response of the naturally-occurring water vapor in the received sample gas is dampened. The dampening may be performed by passing the sample gas though a portion of a gas dryer 122 (e.g., a sample flow segment of a Nafion® sulfonated tetrafluoroethylene based fluoropolymer-copolymer membrane gas dryer, or simply a "Nafion® dryer"). Alternatively, a variety of different types of gas dryers may be employed. The gas dryer 122 may dampen time response of the naturally-occurring water vapor, while having little effect on sample molecular hydrogen. In a sense, the gas dryer 122 serves a role similar to a low pass filter in the field of electronics. The gas dryer 122 also removes some naturally-occurring water vapor from the sample gas. However, a substantial varying amount of naturally-occurring water vapor typically will still remain.

For example, such varying amount may be as high as 1,000 ppm. At step 130, hydrogen in the original sample gas is converted to water vapor (i.e., sample hydrogen-derived water vapor) to produce converted sample gas. The conversion may be performed by catalyzed oxidation in a catalytic oven 132 using oxygen naturally present in the sample gas (or added thereto for this purpose). The catalyst may be a platinum (Pt), palladium (Pd), nickel (Ni) or other metallic surface heated to a sufficiently high temperature (e.g., heated to 100° to 200° Celsius (C) or more). The concentration of the sample hydrogen-derived water vapor typically will be far less than the concentration of naturally-occurring water vapor, such that the naturally-occurring water vapor is the dominant water vapor component over the catalyst. If the water vapor mixing ratio over the catalyst changes, the conversion time constant of the catalyst changes. Should the water vapor mixing ratio over the catalyst becomes very low (e.g., approaches 0 ppm), the conversion time constant may increase dramatically (e.g., to be greater than 1 or 2 min), introducing delay and thereby preventing very high speed detection (i.e., response times less than or equal to 10 s).

At step 140, flow of the converted sample gas is controlled to reduce pressure. The flow control may be performed by a flow controller 142 (e.g., a critical orifice).

At step 150, water vapor in the converted sample gas is measured to produce a water vapor signal. The measuring may be performed by an optical detection cell 152 that employs optical absorption spectroscopy (e.g., laser absorption spectroscopy, non-dispersive infrared (NDIR) absorption spectroscopy, etc.) or another type of detection to measure the water vapor concentration.

The water vapor signal includes two components in the time domain: a component derived from naturally-occurring water vapor referred to herein as the "naturally-occurring water vapor signal" and a component derived from sample hydrogen-derived water vapor referred to herein as the "sample hydrogen-derived water vapor signal." The naturally-occurring water vapor signal typically only varies over long time periods (e.g., time periods greater than a 1 min) and has a significant offset. The sample hydrogen-derived water vapor typically varies over short time periods (e.g., time periods of less than 1 s) if there is sufficient other water vapor present, since it is unaffected by the dampening produced by the gas dryer 122 (e.g., Nafion® dryer), and has little offset.

At step 160, the converted sample gas passes through other structures of the optical hydrogen detector 102. The other structures may include another portion of the gas dryer 162 (e.g., a low-pressure counter flow segment of the Nafion® dryer), and a vacuum pump 172 that pulls the sample gas through the optical hydrogen detector 102.

At step 170, the converted sample gas exits the optical hydrogen detector 102. The converted sample gas may pass out an outlet 174.

In parallel, at step 180, the water vapor signal is separated in the time domain into the naturally-occurring water vapor signal and the sample hydrogen-derived water vapor signal. The separation may be performed by a processor 182 that includes executable instructions (code) that implement digital signal processing (DSP) techniques. A hydrogen signal is then produced that indicates concentration of sample molecular hydrogen in the sample gas, based on the sample hydrogen-derived water vapor signal (e.g., simply using the sample hydrogen-derived water vapor signal as the hydrogen signal or applying additional adjustments or compensations thereto to produce the hydrogen signal).

As the water vapor mixing ratio over the catalyst of the catalytic oven 132 varies (e.g., due to changes in atmospheric conditions leading to changes in naturally-occurring water vapor which is the dominant component), sensitivity of the sample hydrogen-derived water vapor signal and thereby the hydrogen signal varies. If the naturally-occurring water vapor mixing ratio over the catalyst becomes high (e.g., over 10 ppm), sensitivity may decrease significantly due to the presence of a large background of water vapor that makes separation of the water vapor signal difficult, thereby preventing very high sensitivity detection (i.e., detection of concentrations less than or equal to 10 ppb).

At step 190, the hydrogen signal is output. For example, the processor 182 may store it in a memory, pass it to another instrument, use it to generate a display in a user-interface of the optical hydrogen detector 102 itself, etc.

As mentioned above, there is an apparent tension between detection speed and detection sensitivity related to the water vapor mixing ratio over the catalyst. As a result, the optical hydrogen detector 102 discussed in relation to FIGS. 1A and 1B that allows water vapor in the sample gas to vary over time within a wide range (e.g., due to changes in atmospheric conditions leading to changes in naturally-occurring water vapor which is the dominant component) may struggle to consistently achieve both very high speed and very high sensitivity detection of molecular hydrogen. When the water vapor mixing ratio over the catalyst rises, variations in sample molecular hydrogen can be converted more rapidly to variations in sample hydrogen-derived water vapor increasing speed, but detection sensitivity is lowered. When the water vapor mixing ratio over the catalyst decreases, the conversion time constant increases reducing speed, but detection sensitivity rises.

Performance of the example optical hydrogen detector 102 discussed in relation to FIGS. 1A and 1B may be improved by controlling water vapor level over the catalyst to provide a substantially stable level of water vapor (or more specifically, level of "controlled water vapor") at a target mixing ratio. By causing the level of controlled water vapor over the catalyst to be substantially equal to a target mixing ratio that is not too low as to impair response time, and not too high as to impair sensitivity, both very high speed and very high sensitivity can be achieved.

Figure 2:
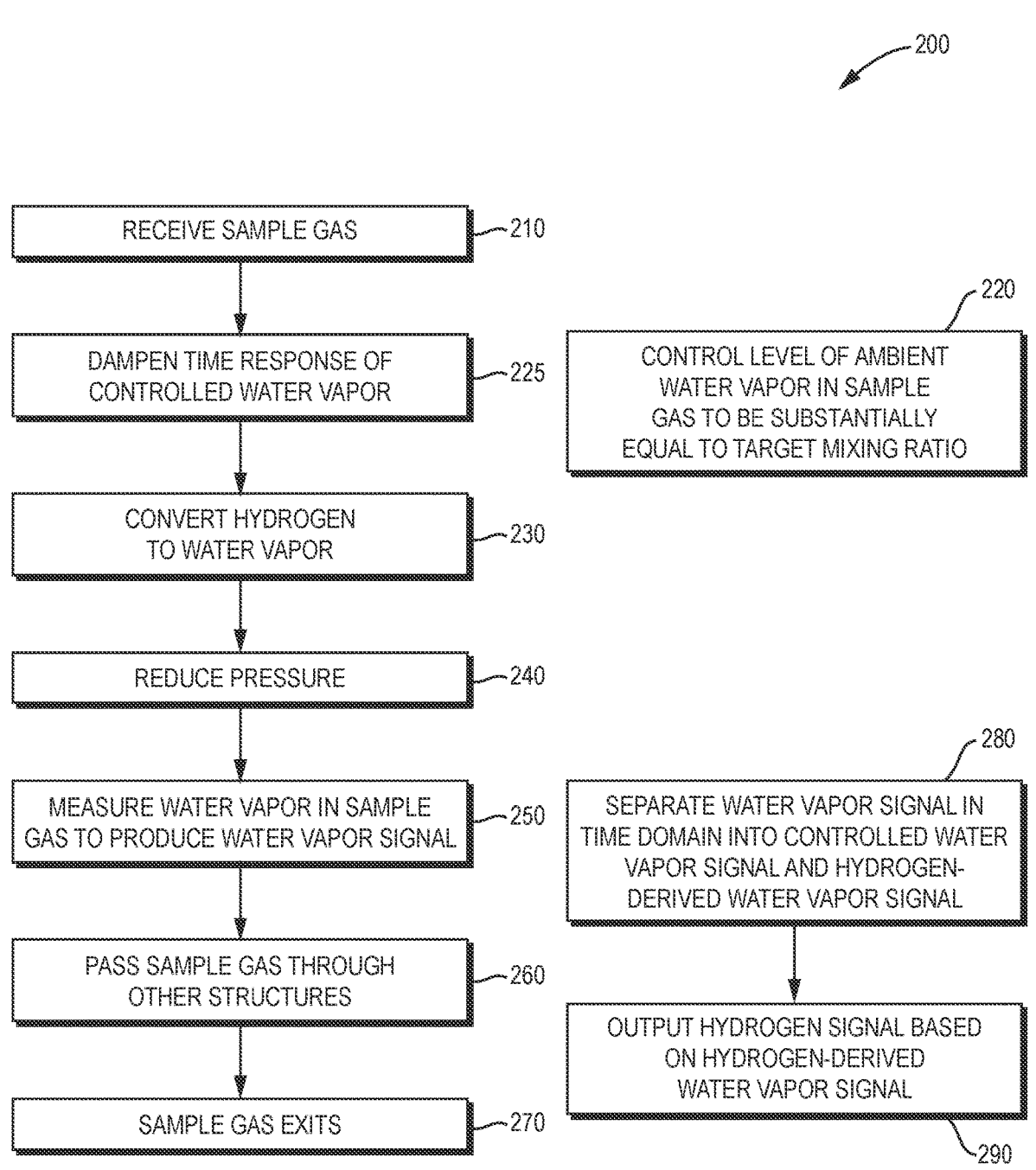
FIG. 2 is a flow diagram of an example generalized sequence of steps for detecting molecular hydrogen in which a level of water vapor over a catalyst is controlled to be substantially stable at a target mixing ratio.

FIG. 2 is a flow diagram of an example generalized sequence of steps 200 for detecting molecular hydrogen in which water vapor level over a catalyst is controlled to be substantially stable at a target mixing ratio. Where steps are similar to those in FIG. 1A, reference may be made to the above description and details omitted.

At step 210, an improved optical hydrogen detector receives sample gas (e.g., ambient air) that includes naturally-occurring water vapor and sample molecular hydrogen.

At step 220, the level of water vapor in the sample gas (or more specifically, the level of "controlled water vapor") is controlled to be substantially equal to a target mixing ratio that is not too low as to impair response time, and not too high as to impair sensitivity. Such a target mixing ratio may be selected as a value between 1 part per million (ppm) and 60 ppm, and preferably as a value between 3 ppm and 30 ppm, such as ppm. The target mixing ratio may be achieved through water reduction. In a water reduction approach, water vapor is precisely removed from the sample gas to achieve the target mixing ratio. Alternatively, the target mixing ratio may be achieved through water addition. In a water addition approach, substantially all the water vapor is removed from the sample gas and then a precise amount of water vapor is added back to achieve the target mixing ratio. In a preferred implementation, the target mixing ratio is achieved through hydrogen addition. In a hydrogen addition approach, instead of directly adding water vapor, a precise amount of hydrogen (or a hydrogen-containing water-convertible species) is added to the sample gas. Substantially all the water vapor is removed. Then, the hydrogen (or a hydrogen-containing water-convertible species) is converted by the catalyst to water vapor to achieve the target mixing ratio. Water vapor that is a product of the natural environment or produced from sources other than the molecular hydrogen being measured (i.e., naturally-occurring water vapor) once controlled through water reduction, water addition, hydrogen-addition or other control techniques is referred to herein as "controlled water vapor."

At step 225, which may occur at least partially before, simultaneous to, or after step 220, the time response of the controlled water vapor in the sample gas is dampened. The dampening may be performed by passing the sample gas though a portion of a gas dryer (e.g., a "Nafion® dryer"), similar to as in FIGS. 1A and 1i, or may otherwise be a result of how the controlled water vapor is produced.

At step 230, hydrogen (the original hydrogen and added hydrogen or hydrogen-containing water-convertible species in the case of a hydrogen addition approach) in the sample gas is converted to water vapor to produce converted sample gas. The conversion may be performed by catalyzed oxidation in a catalytic oven, similar to as in FIGS. 1A and 1B. Because the level of water vapor (or more specifically, "controlled water vapor") is substantially stably maintained over the catalyst at the target mixing ratio, it will not become so low such that the conversion time constant increases dramatically thereby preventing very high speed detection (i.e., response times less than or equal to 10 s).

At step 240, flow of the converted sample gas is controlled to reduce pressure, similar to as in FIGS. 1A and 1B.

At step 250, water vapor in the converted sample gas is measured to produce a water vapor signal.

The water vapor signal includes two components in the time domain: a component derived from the controlled water vapor referred to herein as the "controlled-water vapor signal" and a sample hydrogen-derived water vapor signal. The measuring may be performed by an optical detection cell that employs optical absorption spectroscopy, similar to as in FIGS. 1A and 1B.

At step 260, the converted sample gas passes through other structures of the optical hydrogen detector, similar to as in FIGS. 1A and 1B.

At step 270, the converted sample gas exits the optical hydrogen detector, similar to as in FIGS. 1A and 1B.

In parallel, at step 280, the water vapor signal is separated in the time domain into the controlled water vapor signal and the sample hydrogen-derived water vapor signal, for example, by code executing on a processor 282 implementing DSP techniques. A hydrogen signal that indicates concentration of sample molecular hydrogen in the sample gas, is then produced based on the sample hydrogen-derived water vapor signal, similar to as in FIGS. 1A and 1B. Because the level of water vapor (or more specifically, level of "controlled water vapor") was substantially stably maintained over the catalyst at the target mixing ratio, there will not be too large a background of water vapor to impede separation of the water vapor signal, and very high sensitivity detection (i.e., detection of concentrations less than or equal to 10 ppb) can be achieved.

Finally, at step 290, the hydrogen signal is output (e.g., stored in a memory, passed to another instrument, used to generate a display in a user-interface of the optical hydrogen detector itself, etc.).

Figure 3A:
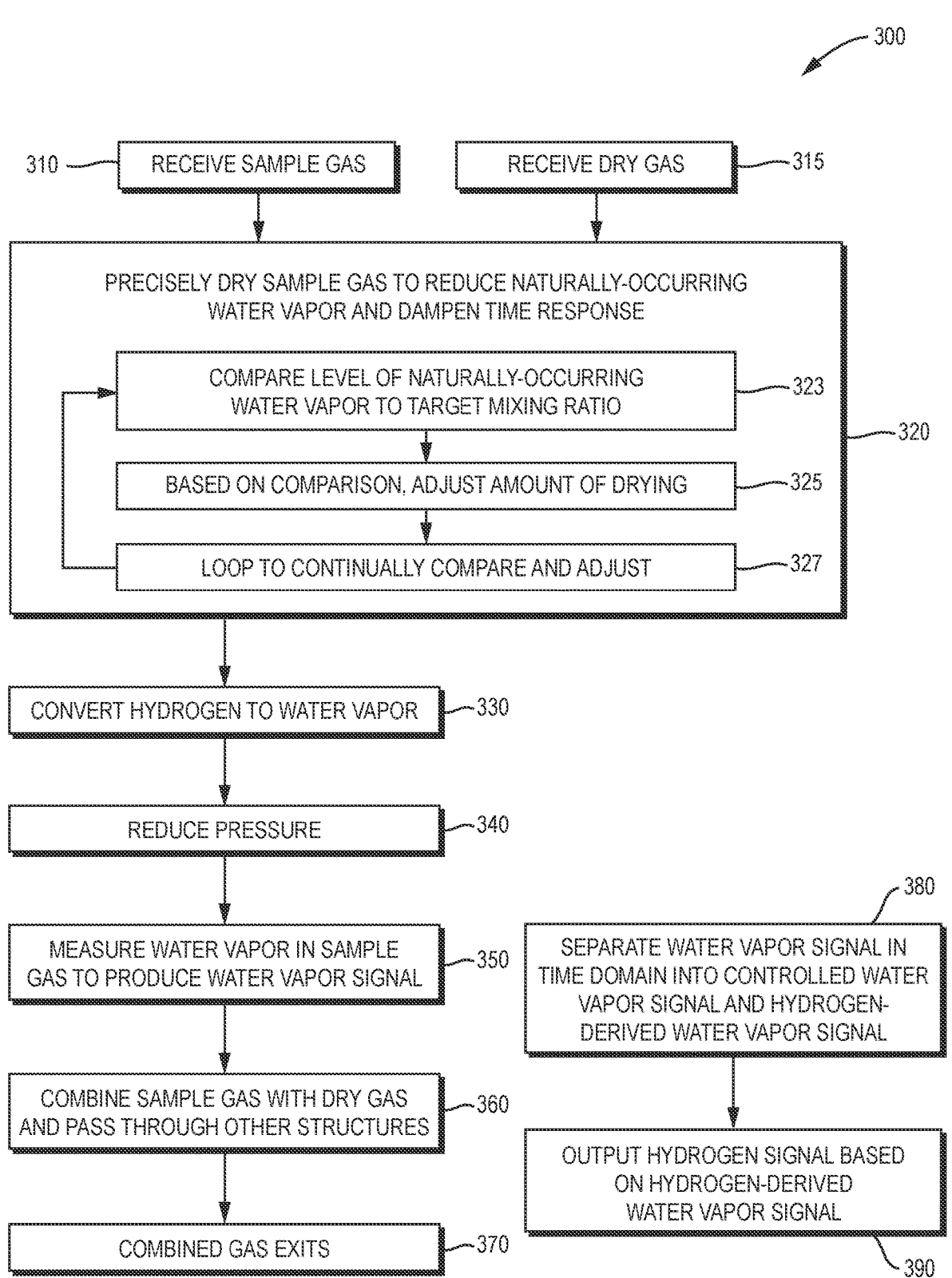
FIG. 3A is a flow diagram of an example sequence of steps for detecting molecular hydrogen in which a level of water vapor over a catalyst is controlled using a water reduction approach where water vapor is precisely removed from the sample gas to achieve the target mixing ratio.
Figure 3B:
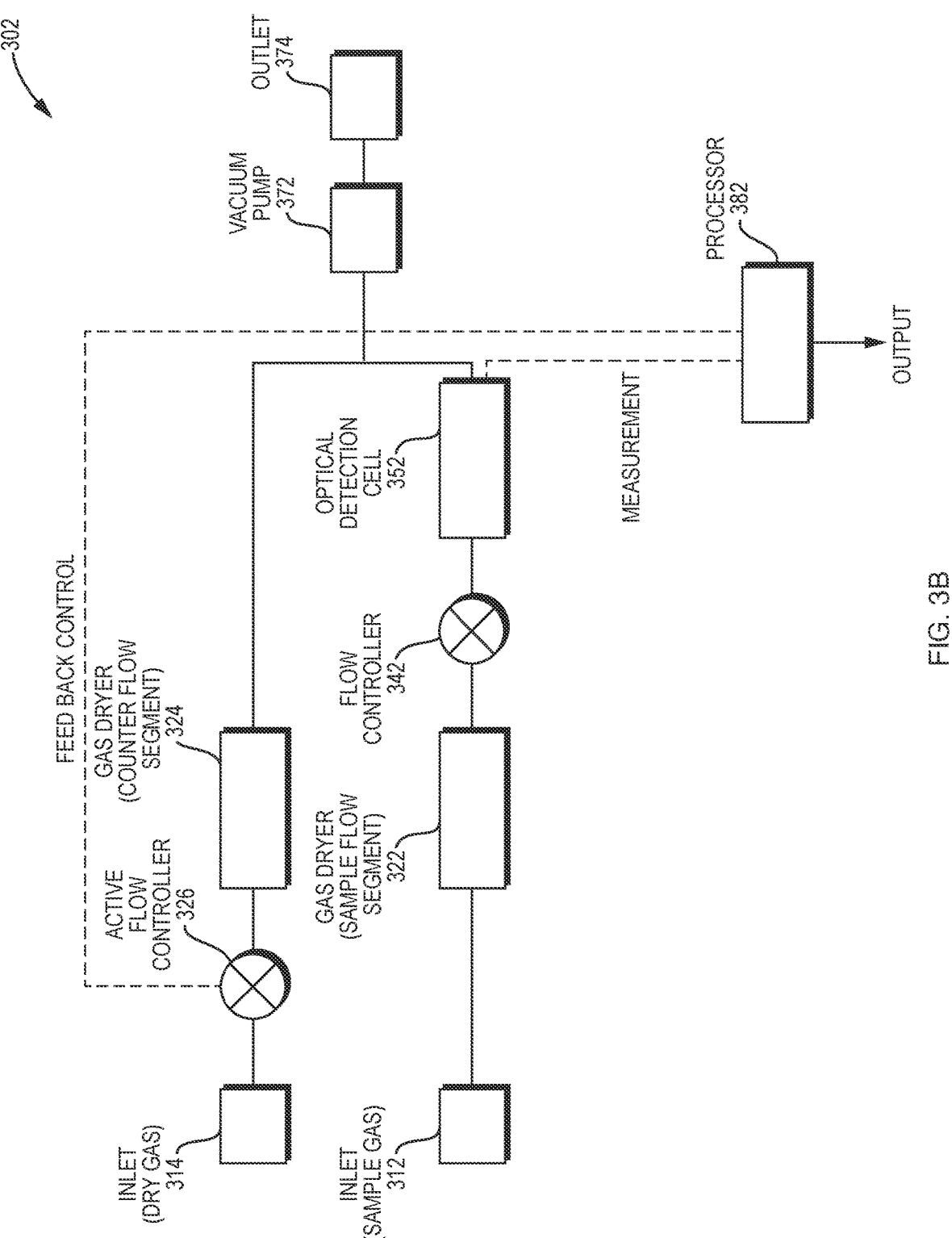
FIG. 3B is a block diagram of an example improved optical hydrogen detector with components that may implement the sequence of steps in FIG. 3A.

FIG. 3A is a flow diagram of an example sequence of steps 300 for detecting molecular hydrogen in which water vapor level over a catalyst is controlled using a water reduction approach where water vapor is precisely removed from the sample gas to achieve the target mixing ratio. FIG. 3B is a block diagram of an example improved optical hydrogen detector 302 with components that may implement the sequence of steps in FIG. 3A. Where steps and components are similar to those in FIGS. 1A and 1B, reference may be made to the above description and details omitted.

At step 310, the improved optical hydrogen detector 302 receives sample gas (e.g., ambient air) that includes naturally-occurring water vapor and sample molecular hydrogen. The sample gas may be received via an inlet 312, as in FIGS. 1A and 1B. In this embodiment, it may be assumed that the concentration of naturally-occurring water vapor in the sample gas received at the inlet 312 is substantially greater than the target mixing ratio.

At step 315, which may occur simultaneously to step 310, the optical hydrogen detector 302 receives dry gas (e.g., dry zero air that includes less than 1 ppm of water vapor). The dry gas may be received via another inlet 314. While not shown, the dry gas may have been previously prepared using a gas dryer or other apparatus, for example, one or more molecular sieves.

At step 320, the sample gas is both precisely dried to reduce concentration of water vapor to be substantially equal to the target mixing ratio, and the time response of the remaining naturally-occurring water vapor (now being "controlled water vapor") in the sample gas is dampened. The precise drying and dampening may be performed by passing the sample gas though a portion of a gas dryer 322 (e.g., a "Nafion® dryer"). The gas dryer may be similar to the one used in FIGS. 1A and 1B, however may be longer and/or include an increased number of filaments such that it is able to achieve low concentrations.

The precise drying may be achieved using a control feedback loop that manages flow of the dry gas through another portion of the gas dryer 324 (e.g., manages flow of the dry gas through a low-pressure counter flow segment of the Nafion® dryer). At sub-step 323, the level of controlled water vapor in the optical detection cell 352 is compared to the target mixing ratio. This may be performed by the processor 382 by accessing the water vapor signal that is produced as part of step 350, discussed in more detail below, and comparing at least a portion of it to the target mixing ratio. At sub-step 325, based on the comparison, the amount of drying applied to the sample gas is adjusted. This may be performed by the processor 382 sending feedback control signals to a flow controller 326 disposed between the dry gas inlet 314 and the other portion of the gas dryer 324 (e.g., the low-pressure counter flow segment of the Nafion® dryer) to increase flow of dry gas if the level of controlled water vapor is above the target mixing ratio and decrease flow of dry gas if the level of water vapor is below the target mixing ratio. At sub-step 327, execution loops back to sub-step 323, such that the level of controlled water vapor is continually compared, and the amount of drying adjusted, to maintain a substantially stable level of controlled water vapor at the target mixing ratio.

At step 330, hydrogen in the sample gas is converted to water vapor to produce converted sample gas. The conversion may be performed by catalyzed oxidation in a catalytic oven 332, similar to in FIGS. 1A and 1B. Because the level of controlled water vapor is substantially stably maintained over the catalyst at the target mixing ratio, it will not become so low such that the conversion time constant increases dramatically thereby preventing very high speed detection.

At step 340, flow of the converted sample gas is controlled to reduce pressure. The flow control may be performed by a flow controller 342 (e.g., a critical orifice), similar to as in FIGS. 1A and 1B.

At step 350, water vapor in the converted sample gas is measured to produce a water vapor signal. The water vapor signal is used as part of the control feedback loop discussed above in relation to sub-steps 313-317. The water vapor signal includes a controlled water vapor signal and a sample hydrogen-derived water vapor signal, which may be separated as discussed below. The measuring may be performed by an optical detection cell 352 that employs optical absorption spectroscopy, similar to as in FIGS. 1A and 1B.

At step 360, the converted sample gas is combined with the used dry gas and passed through other structures of the optical hydrogen detector 302. The other structures may include a vacuum pump 372 that pulls the combined gas through the optical hydrogen detector 302.

At step 370, the combined gas exits the optical hydrogen detector 302. The combined gas may pass out an outlet 374.

In parallel, at step 380, the water vapor signal is separated in the time domain into the controlled water vapor signal and the sample hydrogen-derived water vapor signal, for example, by code executing on the processor 382 implementing DSP techniques. The sample hydrogen-derived water vapor signal is used to produce a hydrogen signal that indicates concentration of sample molecular hydrogen in the sample gas, similar to as in FIGS. 1A and 1B. Because the level of controlled water vapor was substantially stably maintained over the catalyst at the target mixing ratio, there will not be a large background of water vapor to impede separation of the water vapor signal, and very high sensitivity detection can be achieved.

Finally, at step 390, the hydrogen signal is output (e.g., stored in a memory, passed to another instrument, used to generate a display in a user-interface of the optical hydrogen detector itself, etc.).

Figure 4A:
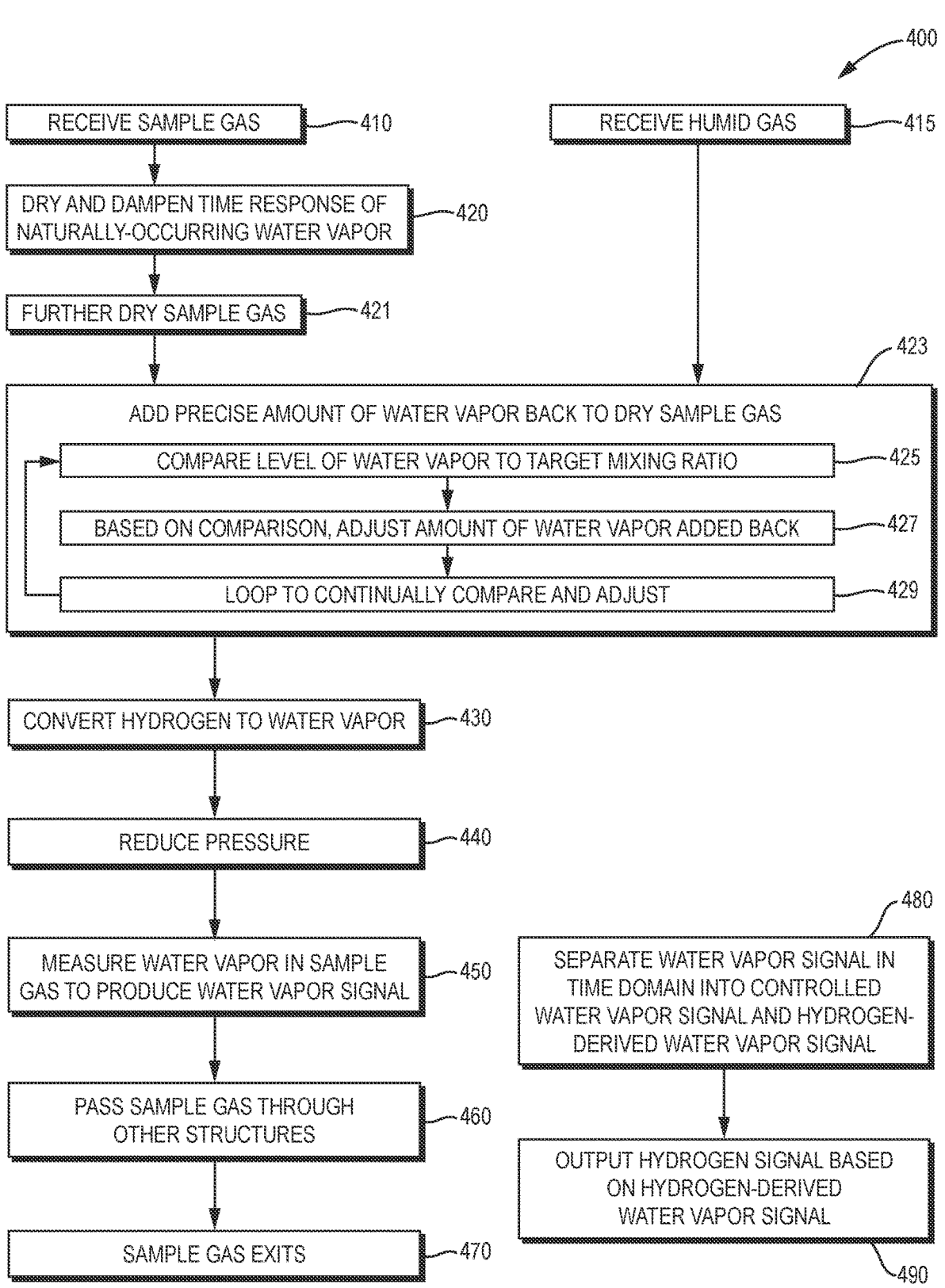
FIG. 4A is a flow diagram of an example sequence of steps for detecting molecular hydrogen in which a level of water vapor over a catalyst is controlled using a water addition approach where substantially all the water vapor is removed from the sample gas and a precise amount of water vapor is then added back to achieve the target mixing ratio.
Figure 4B:
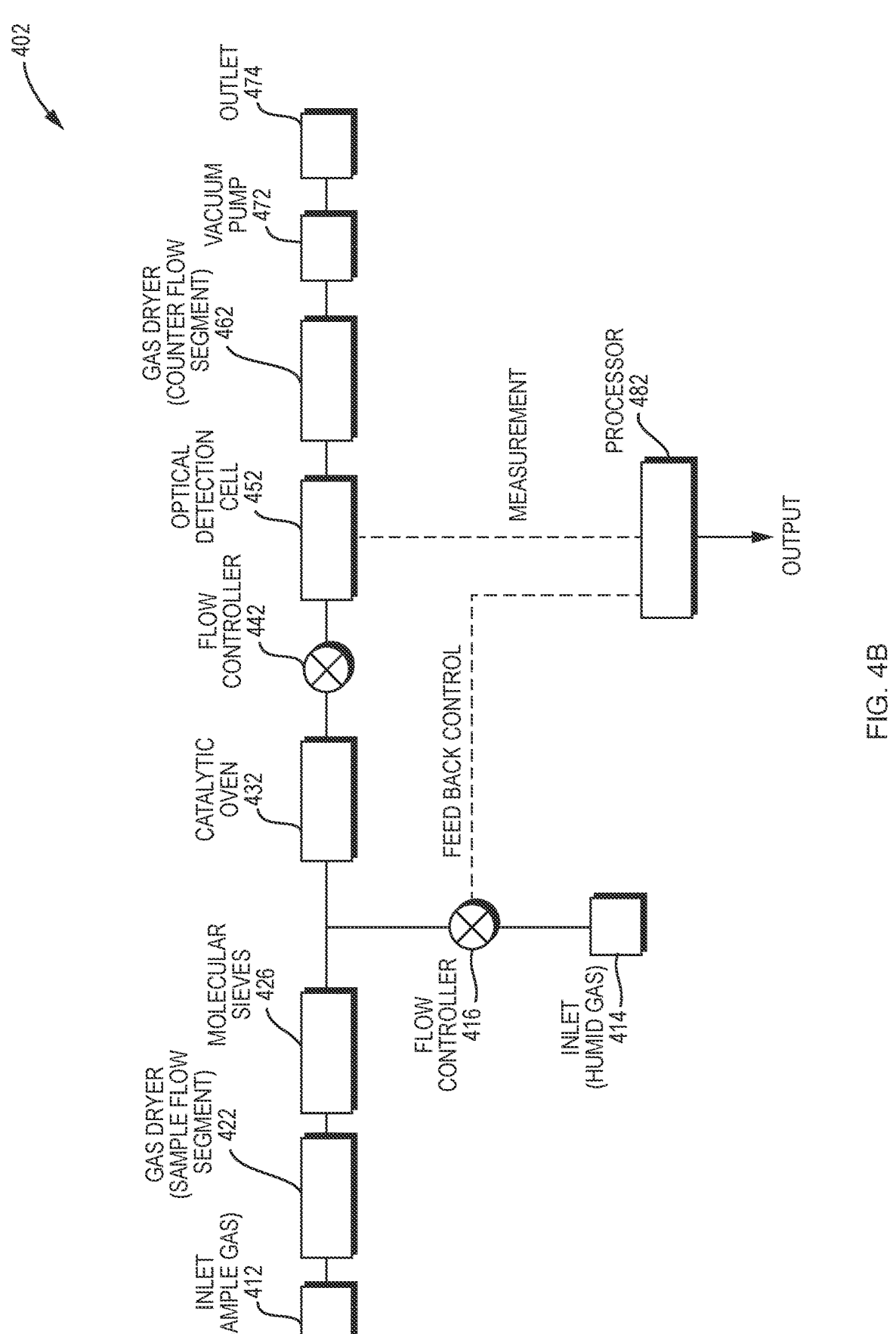
FIG. 4B is a block diagram of an example improved optical hydrogen detector with components that may implement the sequence of steps in FIG. 4A.

FIG. 4A is a flow diagram of an example sequence of steps 400 for detecting molecular hydrogen in which water vapor level over a catalyst is controlled using a water addition approach where substantially all the water vapor is removed from the sample gas and a precise amount of water vapor is then added back to achieve the target mixing ratio. FIG. 4B is a block diagram of an example improved optical hydrogen detector 402 with components that may implement the sequence of steps in FIG. 4A. Where steps and components are similar to those in FIGS. 1A and 1B, reference may be made to the above description and details omitted.

At step 410, the improved optical hydrogen detector 402 receives sample gas (e.g., ambient air) that includes naturally-occurring water vapor and sample molecular hydrogen. The sample gas may be received via an inlet 412, as in FIGS. 1A and 1B.

At step 415, which may occur simultaneously to step 410, the optical hydrogen detector 402 receives humid gas (e.g., humid zero air). The humid gas may be received via another inlet 414. While not shown, the humid gas may have been previously prepared by a dew point generator or water bubbler that passes a gas stream (e.g., zero air) over or through a water reservoir which is held at a fixed temperature.

At step 420, the sample gas is dried and the time response of the naturally-occurring water vapor in the sample gas is dampened. The drying and dampening may be performed by passing the sample gas though a portion of a gas dryer 422 (e.g., a "Nafion® dryer"). The gas dryer 422 also removes some naturally-occurring water vapor from the sample gas. However, a substantial amount of naturally-occurring water vapor typically will still remain (e.g., about 200 to 1000 ppm). The gas dryer may be similar to the one used in FIGS. 1A and 1B.

At step 421, the sample gas is further dried, removing additional naturally-occurring water vapor to produce dry sample gas (i.e., sample gas with a water vapor mixing ratio less than 1 ppm). The further drying may be performed by passing the sample gas through one or more molecular sieves 426. The molecular sieves 426 may be 3 angstrom (A) molecular sieves maintained at room temperature. Alternatively, the sieves may be cooled (e.g., to –78° C.) using a cooler or dry ice. The cooling may assist the molecular sieves 426 in both removing water vapor and other molecules (e.g., acetylene, volatile organic compounds, etc.) that may produce water if they reach the catalyst.

At step 423, a precise amount of water vapor is added back to the dry sample gas to achieve the target mixing ratio, by mixing a specific amount of humid gas (e.g., humid zero air) into the sample gas. The water vapor becomes additional water vapor and its time response is inherently dampened due to the manner of its addition. Any remaining naturally-occurring water vapor and the added additional water vapor collectively form "controlled water vapor."

The precise addition may be achieved using a control feedback loop that manages flow of the humid gas. A control feedback loop is useful because water is sticky and has temperature dependent vapor pressure, which may hinder the precise addition of water vapor using techniques based on flow control and water vapor pressure control. At sub-step 425, the level of controlled water vapor in the optical detection cell 452 is compared to the target mixing ratio. This may be performed by the processor 482 by accessing the water vapor signal that is produced as part of step 450, discussed in more detail below, and comparing at least a portion of it to the target mixing ratio. At sub-step 427, based on the comparison, the amount of water vapor added back to the sample gas is adjusted. This may be performed by the processor 482 sending feedback control signals to a flow controller 416 disposed between the humid gas inlet 414 and the junction with the sample gas flow to increase flow of humid gas if the level of controlled water vapor is below the target mixing ratio, and to decrease flow of humid gas if the level of controlled water vapor is above the target mixing ratio. Typically, only a very small amount of humid gas needs to be added to reach the target mixing ratio (e.g., the flow rate of the sample gas typically will be at least 100 times greater than the flow rate of the humid gas). At sub-step 429, execution loops back to sub-step 425, such that the level of controlled water vapor is continually compared and the amount of water vapor added back is adjusted to maintain a substantially stable level of controlled water vapor at the target mixing ratio.

At step 430, hydrogen in the sample gas is converted to water vapor to produce converted sample gas. The conversion may be performed by catalyzed oxidation in a catalytic oven 432, similar to in FIGS. 1A and 1B. Because the level of controlled water vapor is substantially stably maintained over the catalyst at the target mixing ratio, it will not become so low such that the conversion time constant increases dramatically thereby preventing very high speed detection.

At step 440, flow of the converted sample gas is controlled to reduce pressure. The flow control may be performed by a flow controller 442 (e.g., a critical orifice), similar to as in FIGS. 1A and 1B.

At step 450, water vapor in the converted sample gas is measured to produce a water vapor signal. The water vapor signal is used as part of the control feedback loop discussed above in relation to sub-steps 425-429. The water vapor signal includes a controlled water vapor signal and a sample hydrogen-derived water vapor signal. The measuring may be performed by an optical detection cell 452 that employs optical absorption spectroscopy, similar to as in FIGS. 1A and 1B.

At step 460, the converted sample gas passes through other structures of the optical hydrogen detector 402. The other structures may include another portion of the gas dryer 462 (e.g., a low-pressure counter flow segment of the Nafion® dryer), and a vacuum pump 472 that pulls the sample gas through the optical hydrogen detector 402.

At step 470, the converted sample gas exits the optical hydrogen detector 402. The converted sample gas may pass out an outlet 474.

In parallel, at step 480, the water vapor signal is separated in the time domain into the controlled water vapor signal and the sample hydrogen-derived water vapor signal, for example, by code executing on the processor 482 implementing DSP techniques. The sample hydrogen-derived water vapor signal is used to produce a hydrogen signal that indicates concentration of sample molecular hydrogen in the sample gas, similar to as in FIGS. 1A and 1B. Because the level of controlled water vapor was substantially stably maintained over the catalyst at the target mixing ratio, there will not be a large background of water vapor to impede separation of the water vapor signal, and very high sensitivity detection can be achieved.

Finally, at step 490, the hydrogen signal is output (e.g., stored in a memory, passed to another instrument, used to generate a display in a user-interface of the optical hydrogen detector itself, etc.).

FIG. 5A is a flow diagram of an example sequence of steps 500 for detecting molecular hydrogen in which water vapor level over a catalyst is controlled using a hydrogen addition approach where a precise amount of hydrogen (or a hydrogen-containing water-convertible species) is added to the sample gas, substantially all the water vapor is removed from the sample gas, and the hydrogen (or a hydrogen-containing water-convertible species) is converted by the catalyst to water vapor to achieve the target mixing ratio. FIG. 5B is a block diagram of an example improved optical hydrogen detector 502 with components that may implement the sequence of steps in FIG. 5A. Where steps and components are similar to those in FIGS. 1A and 1B, reference may be made to the above description and details omitted.

At step 510, the improved optical hydrogen detector 502 receives sample gas (e.g., ambient air) that includes naturally-occurring water vapor and sample molecular hydrogen. The sample gas may be received via an inlet 512, as in FIGS. 1A and 1B.

At step 515, which may occur simultaneously to step 510, the optical hydrogen detector 502 receives a mixture containing a precise and stable amount of molecular hydrogen (or a hydrogen-containing water-convertible species) in a dry buffer gas (i.e., a buffer gas having a water vapor mixing ration less than 1 ppm). In various implementations, the hydrogen-containing water-convertible species may be acetylene, a volatile organic compound, or another species that when oxidized produces water vapor, and the dry buffer gas may be dry nitrogen, dry air, or another dry gas containing less than 1 ppm water vapor. In one implementation, the mixing ratio of hydrogen in the mixture has a value of about 2,000 ppm. The mixture may be received via another inlet 514, for example, from a reference cylinder (not shown) or other source.

At step 517, a precise amount of hydrogen (or a hydrogen-containing water-convertible species) is added to the sample gas by mixing in a specific amount of the mixture containing molecular hydrogen (or the hydrogen-containing water-convertible species). The precise addition may be achieved using a flow controller 516. While a control feedback loop (similar to as used in the example water reduction and water addition approaches discussed above) may be used, the flow controller may also be statically set, simplifying the optical hydrogen detector 502. Typically, only a very small amount of the mixture needs to be added to the sample gas. In one implementation, where the flow rate of the sample gas has a value of about 1 standard liter per minute (slpm), the flow controller may provide a flow rate of about 0.01 slpm for the mixture.

At step 520, the sample gas is dried and the time response of the naturally-occurring water vapor in the sample gas is dampened. The drying and dampening may be performed by passing the sample gas though a portion of a gas dryer 522 (e.g., a "Nafion® dryer"). The gas dryer may be similar to the one used in FIGS. 1A and 1B.

At step 525, the sample gas (which now also includes added hydrogen or hydrogen containing species) is further dried, removing additional water vapor to produce dry sample gas (i.e., sample gas with a water vapor mixing ratio less than 1 ppm). The further drying may be performed by passing the sample gas through one or more molecular sieves 526. The molecular sieves 526 may be 3A molecular sieves maintained at room temperature.

At step 530, the original sample hydrogen and the added hydrogen (or hydrogen-containing water-convertible species) is converted to water vapor to produce converted sample gas. The conversion may be performed by catalyzed oxidation in a catalytic oven 432, similar to in FIGS. 1A and 1B. As a result of the conversion, the added hydrogen (or hydrogen-containing water-convertible species) becomes additional water vapor which is inherently dampened due to the manner of its creation. The additional water vapor resulting from the conversion of added hydrogen (or hydrogen-containing water-convertible species) is referred to as "converted water vapor."

The mixing ratio of the water vapor after conversion for a case of adding hydrogen may be given as:

$$MR(t)=MR(hm)*F(hm)/F(s)+MR(s)$$

where MR(t) is the mixing ratio of water vapor in the gas exiting the catalytic oven, MR(hm) is the mixing ratio of hydrogen in the mixture being added, F(hm) is the flow rate of the mixture being added, F(s) is the flow rate of the original sample gas, and MR(s) is the mixing ratio of hydrogen in the sample gas before hydrogen addition. The first term in the equation leads to the controlled water vapor signal. The second term is leads to the hydrogen signal that is to be measured. While this equation applies to hydrogen addition, one skilled in the art will appreciate that other equations may be readily formed for other hydrogen-containing water-convertible species.

At step 540, flow of the converted sample gas is controlled to reduce pressure. The flow control may be performed by a flow controller 542 (e.g., a critical orifice), similar to as in FIGS. 1A and 1B.

At step 550, water vapor in the converted sample gas is measured to produce a water vapor signal that includes a controlled water vapor signal and a sample hydrogen-derived water vapor signal. The measuring may be performed by an optical detection cell 552 that employs optical absorption spectroscopy, similar to as in FIGS. 1A and 1B.

At step 560, the converted sample gas passes through other structures of the optical hydrogen detector 502. The other structures may include through another portion of the gas dryer 562 (e.g., a low-pressure counter flow segment of the Nafion® dryer), and a vacuum pump 572 that pulls the sample gas through the optical hydrogen detector 502.

At step 570, the converted sample gas exits the optical hydrogen detector 502. The converted sample gas may pass out an outlet 574.

In parallel, at step 580, the water vapor signal is separated in the time domain into the controlled water vapor signal and the sample hydrogen-derived water vapor signal, for example, by code executing on the processor 582 implementing DSP techniques. The sample hydrogen-derived water vapor signal is used to produce a hydrogen signal that indicates concentration of sample molecular hydrogen in the sample gas, similar to as in FIGS. 1A and 1B. Because the level of controlled water vapor was substantially stably maintained over the catalyst at the target mixing ratio, there will not be a large background of water vapor to impede separation of the water vapor signal, and very high sensitivity detection can be achieved.

Finally, at step 590, the hydrogen signal is output (e.g., stored in a memory, passed to another instrument, used to generate a display in a user-interface of the optical hydrogen detector itself, etc.).

A hydrogen addition approach may have a number of practical advantages over water reduction and direct water addition approaches. Hydrogen may be relatively easily delivered in precise amounts (via the mixture of hydrogen or hydrogen-containing water-convertible species in buffer gas), avoiding a need for continual adjustment via control feedback loops monitoring the total water concentration in the optical detection cell. Issues related to the stickiness and temperature dependent vapor pressure of water may be largely avoided as the added hydrogen or hydrogen-containing water-convertible species does not become water until within the optical detection cell 542. The result is that the optical hydrogen detector 502 may be more robust and reliable, and simpler to manufacture and maintain.

In summary, the above description describes example techniques for achieving very high speed and very high sensitivity optical hydrogen detection by controlling water vapor level over a catalyst used to convert hydrogen in sample gas to water vapor. It should be understood that various adaptations, modifications, extensions, and the like may be readily made to improve the described techniques. While it is described above that functionality may be implemented in a specific manner by specific components, it should be understood that the functionality may also be implemented in different manners by different components. Processing and control operations may be performed in hardware, in software or in various combinations thereof. It should be understood that the ordering of any method steps discussed above may be changed to suit various situations or industry requirements. Absent an explicit indication to the contrary, the order of steps described above may be modified such that a subsequent step occurs before a preceding step, or in parallel to such step. Above all, it should be understood that the above descriptions are meant to be taken only by way of example.

What is claimed is:

1. A method for detecting molecular hydrogen, comprising:

receiving sample gas that includes naturally-occurring water vapor and sample molecular hydrogen;

controlling a level of water vapor in the sample gas to be substantially equal to a target mixing ratio, wherein the target mixing ratio is selected as a value between 1 part per million (ppm) and 60 ppm;

converting hydrogen in the sample gas to additional water vapor to produce converted sample gas;

measuring water vapor in the converted sample gas to produce a water vapor signal;

separating the water vapor signal into a controlled water vapor signal that describes controlled water vapor and a sample hydrogen-derived water vapor signal that describes sample hydrogen-derived water vapor; and outputting a hydrogen signal that describes sample molecular hydrogen in the sample gas that is based on the sample hydrogen-derived water vapor signal.

2. The method of claim 1, wherein the target mixing ratio is selected as a value between 3 ppm and 30 ppm.

3. The method of claim 1, wherein the controlling the level of water vapor in the sample gas is performed by water reduction, and the water reduction comprises:

drying the sample gas;

comparing a measured water vapor mixing ratio to the target mixing ratio; and adjusting an amount of drying applied to the sample gas based on the comparison until the target mixing ratio is achieved.

4. The method of claim 1, wherein the controlling the level of water vapor in the sample gas is performed by water addition, and the water addition comprises:

drying the sample gas to produce dry sample gas;

comparing a measured water vapor mixing ratio to the target mixing ratio; and adjusting an amount of humid gas mixed into the dry sample gas based on the comparison until the target mixing ratio is achieved.

5. The method of claim 1, wherein the controlling the level of water vapor in the sample gas is performed by hydrogen addition, and the hydrogen addition comprises:

drying the sample gas to produce dry sample gas; and adding an amount of a mixture containing hydrogen or a hydrogen-containing water-convertible species to the dry sample gas, wherein the converting also converts the hydrogen or hydrogen-containing water-convertible species of the mixture to controlled water vapor to achieve the target mixing ratio.

6. The method of claim 5, wherein the drying the sample gas to produce dry sample gas is performed prior to the converting.

7. The method of claim 6, wherein the drying is performed after the adding the amount of the mixture to the sample gas.

8. The method of claim 5, wherein a mixing ratio of hydrogen or hydrogen-containing water-convertible species in the mixture is substantially 2,000 parts per million (ppm), the flow rate of the sample gas is substantially 1 standard liter per minute (slpm), and the flow rate of the mixture is substantially 0.01 slpm.

9. The method of claim 1, wherein the dampening time response is performed by a gas dryer, the converting hydrogen is performed by a catalyst in a catalytic oven, and the measuring water vapor in the converted sample gas is performed by an optical detection cell that uses optical absorption spectroscopy.

10. A molecular hydrogen detector, comprising:

an inlet configured to receive sample gas that includes naturally-occurring water vapor and sample molecular hydrogen;

a gas dyer configured to dry the sample gas;

a flow controller configured to add an amount of humid gas to the sample gas or an amount of a mixture containing hydrogen or a hydrogen-containing water-convertible species to the sample gas to produce controlled water vapor, to cause a level of controlled water vapor in the sample gas to be substantially equal to a target mixing ratio;

a catalytic oven including a catalyst configured to convert hydrogen in the sample gas to water vapor to produce converted sample gas;

an optical detection cell configured to use optical absorption spectroscopy to measure water vapor in the converted sample gas to produce a water vapor signal; and a processor configured to separate the water vapor signal into a controlled water vapor signal that describes the controlled water vapor and a sample hydrogen-derived water vapor signal that describes sample hydrogen-derived water vapor and output a hydrogen signal that describes sample molecular hydrogen in the sample gas that is based on the sample hydrogen-derived water vapor signal.

11. The molecular hydrogen detector of claim 10, wherein the target mixing ratio is selected as a value between 3 ppm and 30 ppm.

12. The molecular hydrogen detector of claim 10, further comprising:

one or more molecular sieves configured to also dry the sample gas.

13. The molecular hydrogen detector of claim 10, wherein the flow controller is configured to add the amount of the mixture containing hydrogen or the hydrogen-containing water-convertible species to the sample gas to cause the level of controlled water vapor in the sample gas to be substantially equal to the target mixing ratio, and the catalyst is further configured to convert the hydrogen or the hydrogen-containing water-convertible species of the mixture to controlled water vapor in the converted sample gas.

14. A method for detecting molecular hydrogen, comprising:

receiving sample gas that includes naturally-occurring water vapor and sample molecular hydrogen;

drying the sample gas;

adding an amount of a mixture containing hydrogen or a hydrogen-containing water-convertible species to the sample gas;

converting hydrogen in the sample gas to water vapor to produce converted sample gas having a level of controlled water vapor substantially equal to a target mixing ratio, wherein the converting converts both the sample molecular hydrogen and hydrogen or hydrogen-containing water-convertible species contained in the added mixture to water vapor, and the hydrogen or hydrogen-containing water-convertible species of the added mixture becomes controlled water vapor;

measuring water vapor in the converted sample gas to produce a water vapor signal;

separating the water vapor signal into a controlled water vapor signal that describes the controlled water vapor and a sample hydrogen-derived water vapor signal that describes sample hydrogen-derived water vapor; and outputting a hydrogen signal that describes sample molecular hydrogen in the sample gas that is based on the sample hydrogen-derived water vapor signal.

15. The method of claim 14, wherein the target mixing ratio is selected as a value between 3 ppm and 30 ppm.

16. The method of claim 14, wherein the drying the sample gas is performed prior to the converting.

17. The method of claim 16, wherein the drying the sample gas is performed after the adding the amount of the mixture to the sample gas.

18. The method of claim 14, wherein a mixing ratio of hydrogen or hydrogen-containing water-convertible species in the mixture is substantially 2,000 parts per million (ppm), the flow rate of the sample gas is substantially 1 standard liter per minute (slpm), and the flow rate of the mixture is substantially 0.01 slpm.

19. The method of claim 14, wherein the drying is performed by a gas dryer, the converting hydrogen is performed by a catalyst in a catalytic oven, and the measuring water vapor in the converted sample gas is performed by an optical detection cell that uses optical absorption spectroscopy.

20. A molecular hydrogen detector, comprising:

means for receiving sample gas that includes naturally-occurring water vapor and sample molecular hydrogen;

means for drying the sample gas;

means for adding an amount of a mixture containing hydrogen or a hydrogen-containing water-convertible species to the sample gas;

means for converting hydrogen in the sample gas to water vapor to produce converted sample gas having a level of controlled water vapor substantially equal to a target mixing ratio, wherein the means for converting is configured to convert both the sample molecular hydrogen and hydrogen or hydrogen-containing water-convertible species contained in the added mixture to water vapor, and the hydrogen or hydrogen-containing water-convertible species of the added mixture becomes controlled water vapor;

means for measuring water vapor in the converted sample gas to produce a water vapor signal; and means for separating the water vapor signal into a controlled water vapor signal that describes the controlled water vapor and a sample hydrogen-derived water vapor signal that describes sample hydrogen-derived water vapor, and for outputting a hydrogen signal that describes sample molecular hydrogen in the sample gas that is based on the sample hydrogen-derived water vapor signal.

* * * * *